United States Patent [19]

Sarrine

[11] Patent Number: 4,828,670

[45] Date of Patent: May 9, 1989

[54] ELECTROPHORETIC SUPPORT MEDIUM AND METHOD OF MAKING SAME

[75] Inventor: Robert J. Sarrine, Beaumont, Tex.

[73] Assignee: Helena Laboratories Corporation, Beaumont, Tex.

[21] Appl. No.: 1,499

[22] Filed: Jan. 8, 1987

[51] Int. Cl.⁴ .............................................. G01N 27/26
[52] U.S. Cl. ............................... 204/299 R; 204/182.8
[58] Field of Search ........................... 204/182.8, 299 R

[56] References Cited

U.S. PATENT DOCUMENTS 3,554,894 1/1971 Zemel ................................ 204/182.8
4,310,407 1/1982 Kaneko et al. .................. 204/299 R
4,443,319 4/1984 Chait et al. ...................... 204/299 R

*Primary Examiner*—John F. Niebling
*Assistant Examiner*—John S. Starsiak

*Attorney, Agent, or Firm*—Spencer & Frank

[57] ABSTRACT

An electrophoretic support medium and method of making the same are disclosed for use in the analysis of ionizable compounds to be made by subjecting a sample to an electrical potential. The electrophoretic support medium includes a base sheet having at least one negative electrode and at least one positive electrode deposited thereon in a predetermined pattern. A layer of an electrophoretic gel is adhered to the surface of the base sheet, whereby the electrodes are disposed between the base sheet and the electrophoretic gel layer with the electrodes being in electrical contact with the electrophoretic gel layer. In addition, the electrophoretic gel layer may include a plurality of sample wells formed therein in which a sample to be analyzed may be placed. The method includes depositing the electrodes onto the base sheet before adhering the gel layer thereto.

14 Claims, 1 Drawing Sheet

ELECTROPHORETIC SUPPORT MEDIUM AND METHOD OF MAKING SAME

FIELD OF THE INVENTION

The present invention relates generally to electrophoresis and more particularly to an electrophoretic support medium and method of making the same.

BACKGROUND OF THE INVENTION

It is known that an analysis of ionizable compounds, such as proteins, can be made by subjecting a sample, of for example blood, to an electrical potential as taught in U.S. Pat. Nos. 3,407,133 (Olivia et al.) and 3,479,265 (Elevitch). The sample to be analyzed by electrophoresis is placed on a suitable support medium, such as a gel, of the types disclosed in U.S. Pat. No. 3,725,004 (Johnson et al.). Such support mediums may include, for example: (1) aqueous solutions of agar or agarose as disclosed in U.S. Pat. Nos. 3,281,009 (Blethen), 3,335,127 (Polson), 3,362,884 (Morse) and 3,766,047 (Elevitch); (2) synthetic polymeric gelling agents as disclosed in U.S. Pat. No. 3,046,201 (White et al.); and (3) cellulose and cellulose acetate as disclosed in U.S. Pat. No. 3,360,440 (Haab et al.). Such support mediums require the presence of an electrical potential so as to cause migration of the ionizable compounds to be analyzed. This potential has been accomplished by placing electrodes in contact with the medium as disclosed in U.S. Pat. Nos. 3,407,133 (Olivia et al.) and 3,856,656 (Brink). However, such apparatus are relatively complicated in design and construction, and several limitations are associated therewith. The primary limitation is the result of the heat generated during use which requires cooling by, for example, an ice pack. In addition, the voltage at which such apparatus may operate is limited because of the restricted cooling. Further, because such apparatus operate at high voltages, it is desirable that the electrodes be protected from inadvertent contact during the periods that the studies are being conducted.

SUMMARY OF THE INVENTION

In contrast to the prior art electrophoretic support mediums acknowledged above, this invention provides an electrophoretic support medium which is simple in design and construction and a method of making the same. In addition, because of the simple construction, heat generated during use is readily dissipated and it may operate at higher voltages.

The electrophoretic support medium of the present invention for use in the analysis of ionizable compounds such as, for example, proteins of a sample includes a support base sheet of a nonconductive material having at least two opposed major surfaces. A layer of an electrophoretic gel is adhered to one of the major surfaces of the base sheet. At least one negative electrode and at least one positive electrode are disposed between the base sheet and the electrophoretic gel layer in electrical contact therewith. The positive electrode is spaced apart from the negative electrode a sufficient distance so that when an electrical potential is created, analyzable compounds may migrate through the electrophoretic gel layer towards one of the electrodes.

The method for making an electrophoretic support medium of the present invention includes the initial step of depositing a conductive material on a major surface of a nonconductive base sheet at predetermined areas to form at least one negative electrode and at least one positive electrode thereon. The next step includes adhering a layer of an electrophoretic gel to the major surface of the base sheet having the electrodes deposited thereon, so that the electrodes are disposed between the base sheet and the electrophoretic gel layer in electrical contact with the gel layer.

In the preferred embodiment, a second negative electrode is disposed between the base sheet and the electrophoretic gel layer in electrical contact therewith, and the positive electrode is positioned between the negative electrodes. The electrodes run substantially parallel to one another, and the negative electrodes are in electrical connection with one another.

BRIEF DESCRIPTION OF THE DRAWINGS

The various features, benefits, and advantages of the present invention will become more apparent by reading the following detailed description in conjunction with the drawings where like reference numerals identify corresponding components, and.

DETAILED DESCRIPTION OF THE PREFERRED EMBODIMENTS

Figure 1:
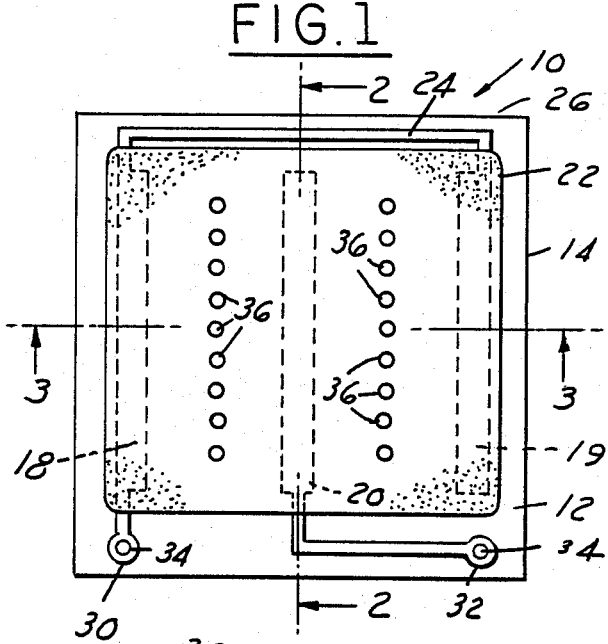
FIG. 1 is a plan view of the electrophoretic support medium of the present invention illustrating the position of the electrodes relative to one another.
Figure 2:
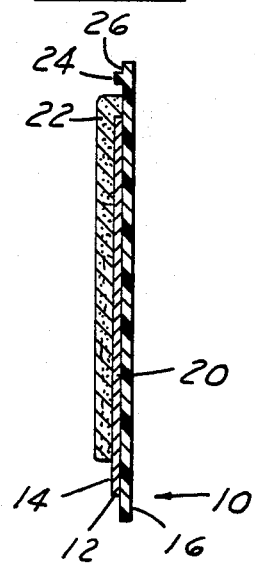
FIG. 2 is a cross-sectional view of the electrophoretic support medium illustrating the details of the layer of the electrophoretic gel, the positive electrode and the base sheet taken in the direction of arrows 2—2 of FIG. 1.
Figure 3:
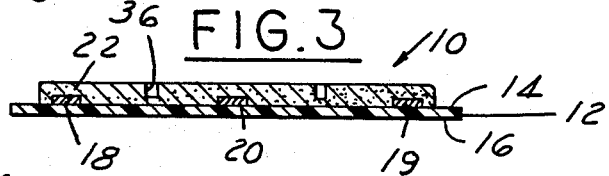
FIG. 3 is a cross-sectional view of the electrophoretic support medium illustrating the details of the layer of electrophoretic gel, the electrodes and base sheet taken in the direction of arrows 3—3 of FIG. 1.
Figure 4:
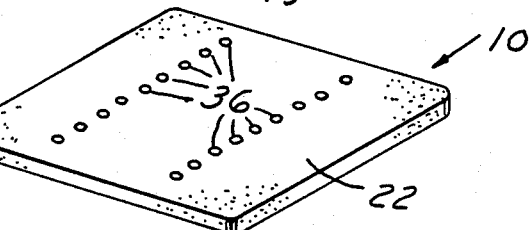
FIG. 4 is an exploded, perspective view of the electrophoretic support medium exposing the electrodes.
Figure 4:
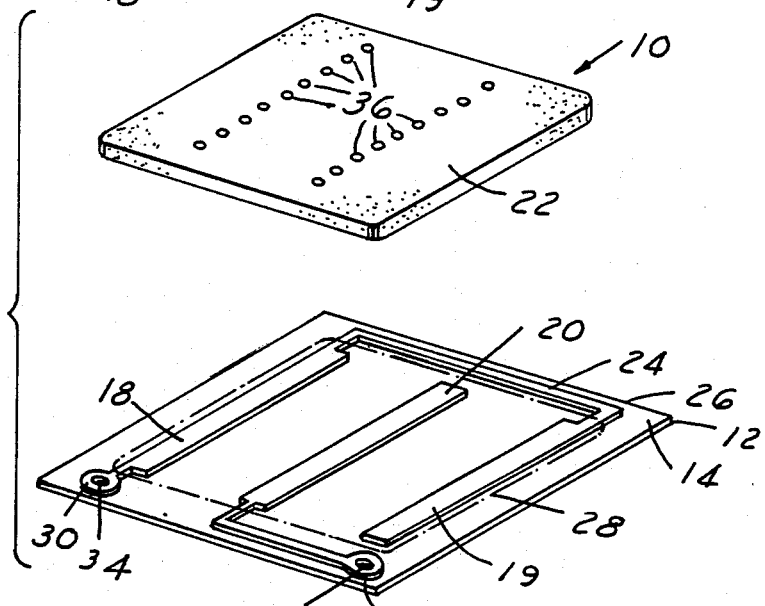

Referring to FIGS. 1, 2 and 3 of the drawing, the electrophoretic support medium of the present invention, generally designated 10, for use in the analysis of ionizable compounds by subjecting a sample to an electrical potential is illustrated. The electrophoretic support medium 10 includes a base sheet 12 having two opposed major surfaces 14 and 16. Associated with one of the surfaces 14 are two negative electrodes 18 and 19 and at least one positive electrode 20 spaced apart from one another to create an electrical potential when connected to an external power supply (not shown). It should be appreciated that only one negative electrode may be utilized. However, two are preferred.

As illustrated, a layer of an electrophoretic gel 22 is adhered to the surface 14 of the base sheet 12 by bonding with the electrodes 18, 19 and 20 disposed therebetween and in electrical contact therewith. The electrodes are spaced a sufficient distance apart so that when an electrical potential is created, the analyzable compounds may migrate through the electrophoretic gel layer towards one of the electrodes. In the preferred embodiment, the electrophoretic gel layer is spaced apart from the peripheral edge of the base sheet. The particular gel is not essential to the present invention and may include any of the mediums of the prior art mentioned hereinabove. However, agarose has been successfully utilized.

The negative electrodes 18 and 19 are interconnected by an electrical lead or connection 24 running along the edge 26 of the base sheet 12 outside of the electrophoretic gel layer 22 so as not to interfere with the electrical potential created within a microporous medium area 28. A negative electrical contact pad 30 is associated with one end of either negative electrode 18 or 19, and a positive electrical contact pad 32 is associated with one end of the positive electrode 20, whereby the contact pads 30 and 32 may be connected to the external power supply. Also, positioning holes 34 are provided in each contact pad for automated system alignment.

In the preferred embodiment, the electrodes 18, 19 and 20, the electrical connection 24, and the contact pads 30 and 32 are deposited directly onto the surface 14 of the base sheet 12. This can be accomplished by a number of methods well-known within the art. However, it has been found that they may be painted onto the surface 14 of the base sheet 12 in the particular pattern desired by utilizing a conductive paint.

A plurality of sample wells 36 are formed in the electrophoretic gel layer 22 and positioned between the negative electrodes 18 and 19 and the positive electrode 20 running substantially parallel to each electrode. Thus, a sample of, for example, feces may be placed in a well to be analyzed.

The electrophoretic support medium 10 of the present invention may be shipped and stored in a container (not shown) as disclosed in U.S. patent application, Ser. No. 930,620 (Attorney Docket No. 366.160, inventor David G. Mayes, and filed on Nov. 14, 1986), the disclosure of which is hereby incorporated by reference. Such containers normally include a top portion and a bottom portion which when closed are sealingly engagable with one another. The bottom portion includes a recess for accommodating the electrophoretic support medium of the present invention, whereby it may be retained in the recess to prevent damage or dehydration. In addition, the electrophoretic support medium 10 of the present invention may be stacked upon one another for shipping and storing when the exposed surface 16 of the base sheet includes a release surface so that the electrophoretic support medium may be peeled away from one another when needed for use.

The particular material of which the base sheet is made is not particularly important to the present invention as long as it is nonconductive. For this reason, polymeric materials have been found to be useful, particularly Mylar ("MYLAR" is a trademark of E. I. DuPont de Nemours & Co. of Wilmington, Del.). However, the particular material is a matter of choice based upon economics and availability.

While the preferred embodiment of the present invention has been described so as to enable one skilled in the art to practice the techniques of the present invention, the preceding description is intended to be exemplary and should not be used to limit the scope of the invention. The scope of the invention should be determined only by reference to the following claims.

What is claimed is:

1. An electrophoretic support medium for use in the analysis of ionizable compounds such as, for example, proteins of a sample, comprising:
   a support base sheet of a nonconductive material having at least two opposed major surfaces;
   a layer of an electrophoretic gel adhered to one of the major surfaces of the base sheet;
   at least one negative electrode disposed between said base sheet and said electrophoretic gel layer in electrical contact therewith;
   at least one positive electrode disposed between said base sheet and said electrophoretic gel layer in electrical contact therewith and spaced apart from said negative electrode a sufficient distance so that when an electrical potential is created, analyzable compounds may migrate through the electrophoretic gel layer towards one of the electrodes said base sheet comprising a peripheral edge and said electrophoretic gel layer being spaced apart from said peripheral edge;
   a second negative electrode disposed between said base sheet and said electrophoretic gel layer in electrical contact therewith;
   electrical contact pads associated with said positive electrode and at least one of said negative electrodes; and plate positioning means associated with said electrical contact pads for automated system alignment.

2. The electrophoretic support medium defined in claim 1, said positive electrode positioned between said first-mentioned negative electrode and said second negative electrode.

3. The electrophoretic support medium defined in claim 2, wherein said electrodes run substantially parallel to one another and said first negative electrode and said second negative electrode are in electrical connection with one another.

4. The electrophoretic support medium defined in claim 1, further comprising a plurality of sample wells formed in said electrophoretic gel layer between said first negative electrode and said positive electrode and between said second negative electrode and said positive electrode in which a sample to be analyzed may be deposited.

5. The electrophoretic support medium defined in claim 1, wherein said negative electrical contact pad is disposed outside of said electrophoretic gel layer between said peripheral edge of said base sheet and said electrophoretic gel layer in electrical connection with said positive electrode.

6. The electrophoretic support medium defined in claim 5, wherein said positive electrical contact pad is disposed outside of said electrophoretic gel layer between said peripheral edge of said base sheet and said electrophoretic gel layer in electrical connection with said positive electrode.

7. The electrophoretic support medium defined in claim 6, wherein said plate positioning means comprises a hole in each of said contact pads.

8. The electrophoretic support medium defined in claim 1, further comprising a plurality of sample wells formed in said electrophoretic gel layer between said negative electrode and said positive electrode in which a sample to be analyzed may be deposited.

9. The electrophoretic support medium defined in claim 1, wherein said electrophoretic gel layer is bonded to said base sheet.

10. A method for making an electrophoretic support medium for use in the analysis of ionizable compounds such as, for example, proteins of a sample, comprising the following steps:
   depositing a conductive material on a major surface of a nonconductive base sheet at predetermined areas to form at least one negative electrode and at least one positive electrode thereon;
   depositing a negative contact pad and a positive contact pad onto said base sheet in electrical contact with the negative electrode and the positive electrode, respectively each of said contact pads including support medium positioning means for automated system alignment; and adhering a layer of an electrophoretic gel to the major surface of said base sheet having said electrodes deposited thereon, so that the electrodes are disposed between the base sheet and the electrophoretic gel layer in electrical contact with said electrophoretic gel layer.

11. The method defined in claim 10, further comprising the step of forming a plurality of sample wells in said electrophoretic gel layer between said negative electrode and said positive electrode in which a sample to be analyzed may be deposited.

12. The method defined in claim 10, wherein said electrodes are painted onto the surface of said base sheet in a predetermined pattern before adhering the electrophoretic gel layer thereto.

13. The method defined in claim 10, wherein said electrophoretic gel layer is spaced apart from a peripheral edge of said base sheet.

14. An electrophoretic support medium for use in the analysis of ionizable compounds such as, for example, proteins of a sample, comprising:

a support base sheet of a nonconductive material having at least two opposed major surfaces;

a layer of an electrophoretic gel adhered to one of the major surfaces of the base sheet;

at least one negative electrode disposed between said base sheet and said electrophoretic gel layer in electrical contact therewith;

at least one positive electrode disposed between said base sheet and said electrophoretic gel layer in electrical contact therewith and spaced apart from said negative electrode a sufficient distance so that when an electrical potential is created, analyzable compounds may migrate through the electrophoretic gel layer towards one of the electrodes;

a second negative electrode disposed between said base sheet and said electrophoretic gel layer in electrical contact therewith; and connection means carried on said base sheet and external to said electrophoretic gel for electrically connecting said first and second negative electrodes.

* * * * *